(12) United States Patent
Stabel et al.

(10) Patent No.: US 8,378,164 B2
(45) Date of Patent: Feb. 19, 2013

(54) METHOD FOR OBTAINING AROMATIC HYDROCARBONS FROM A HYDROCARBON MIXTURE

(75) Inventors: Uwe Stabel, Otterstadt (DE); Petra Deckert, Bammental (DE)

(73) Assignee: BASF SE (DE)

( * ) Notice: Subject to any disclaimer, the term of this patent is extended or adjusted under 35 U.S.C. 154(b) by 269 days.

(21) Appl. No.: 12/680,563

(22) PCT Filed: Sep. 22, 2008

(86) PCT No.: PCT/EP2008/062619
§ 371 (c)(1),
(2), (4) Date: Mar. 27, 2010

(87) PCT Pub. No.: WO2009/043754
PCT Pub. Date: Apr. 9, 2009

(65) Prior Publication Data
US 2010/0228072 A1     Sep. 9, 2010

(30) Foreign Application Priority Data
Sep. 28, 2007   (EP) ..................................... 07117505

(51) Int. Cl.
*C07C 7/08*     (2006.01)
(52) U.S. Cl. .......................... 585/865; 585/860; 585/833
(58) Field of Classification Search ........................ None
See application file for complete search history.

(56) References Cited

U.S. PATENT DOCUMENTS
2010/0305382 A1   12/2010   Stabel et al.

FOREIGN PATENT DOCUMENTS
| EP | 0329958 A2 | 8/1989 |
| WO | WO-2009043753 A1 | 4/2009 |
| WO | WO-2009043754 A1 | 4/2009 |

OTHER PUBLICATIONS

C. Hanson, Solvent Extraction: the Current Position, 1971, Chapter 1 pp. 1-13 and Chapter 14 pp. 495-584, Pergamon Press, Oxford. University of Bradford, U.K.

*Primary Examiner* — Tam M Nguyen
(74) *Attorney, Agent, or Firm* — Novak Druce Connolly Bove + Quigg LLP

(57) ABSTRACT

Processes for obtaining aromatic hydrocarbons from a hydrocarbon mixture a1. Mixture a1 is extractively distilled with extractive solvent a2 producing mixture b1 comprising solvent a2, aromatic hydrocarbons and high boilers, and nonaromatic hydrocarbon mixture b2. Mixture b1 is distilled to aromatic hydrocarbon c1 and solvent comprising high boilers c2. Substream d1 is removed from c2 and c2 is recycled to extractive distillation. Substream d1 is extracted with water producing aqueous phase e1 and organic phase e2. Aqueous phase e1 is distilled and purified solvent a2 is recovered and recycled into extractive distillation of mixture b1. Substream e2' is removed from organic phase e2 and recycled into extractive distillation of mixture b1. The amount of organic phase e2' is such that when d1 comprising solvent, high boilers, water and circulated stream e2' is dispersed, aqueous extract phase e1, forms a disperse phase and organic phase e2 a continuous phase.

6 Claims, 2 Drawing Sheets

METHOD FOR OBTAINING AROMATIC HYDROCARBONS FROM A HYDROCARBON MIXTURE

CROSS REFERENCE TO RELATED APPLICATIONS

Figure 1:
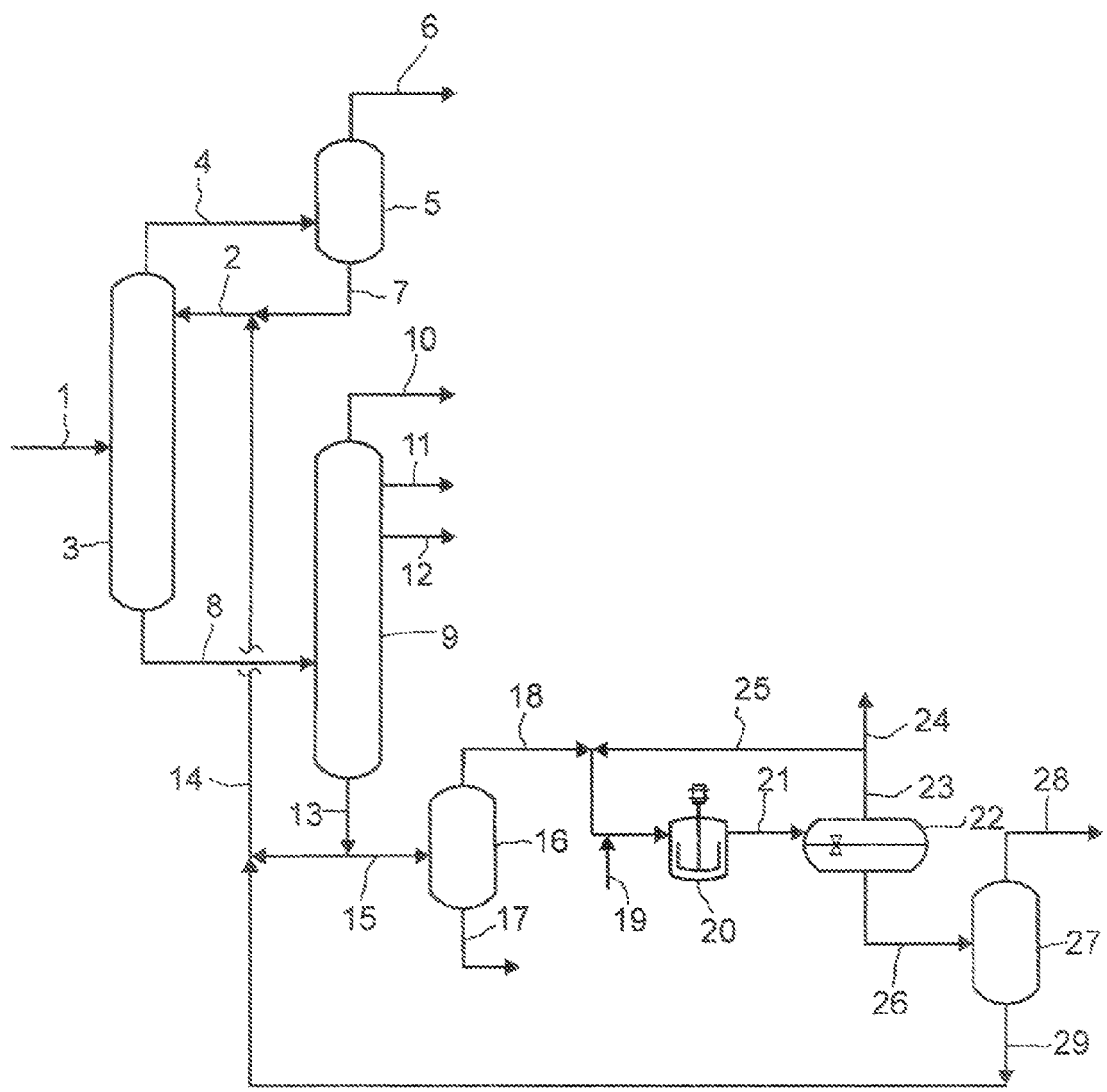

This application is a National Phase filing under 35 U.S.C. §371 of PCT/EP2008/062619 filed in Sep. 22, 2008, which claims priority to Patent Application No. 07117505.3, filed in Europe on Sep. 28, 2007. The entire contents of each of the above-applications are incorporated herein by reference.

DESCRIPTION

The invention relates to a process for obtaining aromatic hydrocarbons from a hydrocarbon mixture which, as well as the aromatic hydrocarbons, comprises nonaromatic hydrocarbons and high-boiling aromatic and nonaromatic hydrocarbons.

The separation of mixtures of aromatics and nonaromatics by extractive distillation is known. Industrial extractive distillation processes use N-methylpyrrolidone, N-formylmorpholine (NFM), dimethylformamide or sulfolane. In the extractive distillation column, the nonaromatics are distilled off, while the aromatics remain in the bottom together with the extractive solvent and are separated therefrom in a subsequent stripping column. Customary aromatics-containing hydrocarbon mixtures stem generally from refineries, cat-crackers and steamcrackers. Extractive distillation is used in particular in the isolation of aromatics from pyrolysis gasolines.

When the hydrocarbon starting mixtures used are hydrocarbon fractions which comprise benzene, toluene, ethylbenzene or xylenes or any mixture thereof as constituents to be extracted, a series of high-boiling aromatic and nonaromatic hydrocarbons with boiling points similar to that of the extractive solvent accumulates in the extractive solvent, which can lead to rapid deterioration in the quality of the extractive solvent. The higher the proportion of high-boiling hydrocarbons, the faster the deterioration in the solvent quality generally takes place. The consequence is a deterioration in the separating performance of the extractive distillation, which can necessitate a rapid exchange of the extractive solvent. Attempts to remove the high-boiling hydrocarbons from the solvent by distillation have not led to a satisfactory result, since some of the high-boiling hydrocarbons boil in the same temperature range as the solvent. Since a distillative separation is virtually impossible, this problem has in the past been solvable only by undertaking a complete exchange of the contaminated solvent after a certain operating time.

EP-A 0 329 958 discloses a process for obtaining an aromatics mixture from a starting hydrocarbon mixture whose boiling range is between 40 and 170° C., and which, as well as nonaromatics, comprises several aromatics, especially benzene, toluene and xylenes, in which the starting hydrocarbon mixture is subjected to an extractive distillation using N-substituted morpholines as the selective solvent. In this process, low-boiling nonaromatics having a boiling range up to approx. 105° C. are distilled off virtually completely, and the relatively high-boiling nonaromatics with a boiling range between approx. 105 and 160° C. predominantly, as the raffinate via the top of the extractive distillation column, while the majority of the aromatics and the remaining nonaromatics are drawn off from the bottom of the extractive distillation column as the extract together with the solvent used. The hydrocarbons of the extract are removed from the extractive solvent by distillation in a downstream stripper column, while the solvent is returned to the stripper column. The process according to EP-A 0 329 958 solves the problem of enrichment of high-boiling aromatics in the extractive solvent by cooling a substream of the extractive solvent drawn off from the stripper column, admixing it with water and introducing it into a phase separator, the high-boiling aromatics present in the solvent being removed from the solvent/water mixture as a lighter upper phase. The solvent/water mixture drawn off from the phase separator is finally separated into its constituents and reused in the process. The process is based on the fact that the high-boiling aromatics and the extractive solvent, especially N-formylmorpholine, have different dissolution properties in water. While the solvent, especially N-formylmorpholine, has unlimited solubility in water, the high-boiling aromatics dissolve in water only in very small amounts. Since the high-boiling aromatics also have a significant density difference compared to the solvent/water mixture, they can be removed from the solvent/water mixture as a light phase in a phase separator.

In the prior art processes, however, a frequent occurrence is that the mixture of extractive solvent/water on the one hand and high-boiling aromatics on the other hand separates only poorly into an upper phase composed of high-boiling aromatics and a lower phase composed of solvent/water mixture.

It is an object of the invention to provide an improved process for obtaining aromatic hydrocarbons from a hydrocarbon mixture which, as well as the aromatic hydrocarbons, comprises nonaromatic hydrocarbons and high-boiling aromatic and nonaromatic hydrocarbons, referred to as "high boilers" for short hereinafter, by means of extractive distillation using N-formylmorpholine, which does not have the disadvantages of the prior art.

The object is achieved by a process for obtaining aromatic hydrocarbons selected from benzene, toluene, xylene and ethylbenzene and mixtures thereof from a hydrocarbon mixture which additionally comprises nonaromatic hydrocarbons and high boilers, comprising the steps of (A) providing a hydrocarbon mixture a1 and an extractive solvent a2 composed of N-formylmorpholine, (B) extractively distilling the hydrocarbon mixture a1 with the extractive solvent to obtain a mixture b1 of extractive solvent and the aromatic hydrocarbons, said mixture comprising high boilers, and a mixture b2 comprising nonaromatic hydrocarbons, (C) distilling the mixture b1 of extractive solvent and aromatic hydrocarbons obtained in step (B) to obtain one or more fractions c1 composed of aromatic hydrocarbons and the extractive solvent c2 which comprises high boilers, (D) removing a substream d1 from the extractive solvent c2 and recycling the extractive solvent c2 into the extractive distillation (B), (E) extracting the substream d1 of the extractive solvent with water to obtain an aqueous extract phase e1 essentially free of high boilers and an organic phase e2 comprising the high boilers, (F) distilling the aqueous extract phase e1 and recovering the extractive solvent a2 in purified form, and recycling the extractive solvent into the extractive distillation (B), which comprises removing a substream e2' from the organic phase e2 comprising the high boilers and recycling it into the extraction of step (E), the amount of the organic phase e2' thus circulated being such that, when the substream d1 composed of extractive solvent comprising high boilers, water and circulated stream e2' is dispersed, the aqueous extract phase e1 essentially freed of high boilers forms as a disperse phase, and the organic phase composed of high boilers e2 as a continuous phase.

It has been found that, surprisingly, the reversal of the direction of dispersion in step (E) allows the phase separation into the aqueous extract phase on the one hand and the organic phase composed of high-boiling aromatic and nonaromatic hydrocarbons on the other hand to be improved significantly. Thus, the phase separation rate is enhanced significantly by the reversal of the direction of dispersion, and the aqueous lower phase comprising the extractive solvent becomes clear. As a result of the improvement in the phase separation, the high boiler impurities from the extractive solvent are more greatly enriched. As a result, the substream d1 which is removed from the extractive solvent c2 comprising high boilers may be of a smaller size. The direction of dispersion can, for example, be reversed by virtue of internal recycling of the organic phase e2 obtained in the phase separation apparatus into the mixing unit.

In general, the volume ratio of the organic high boiler phase to the aqueous extract phase is >0.86 l per l, in order that the organic phase forms as a continuous phase.

NFM present in the organic high boiler phase e2 after phase separation can in turn be recovered by extraction of the phase e2 with water.

High-boiling aromatics which may be present in the hydrocarbon mixture and can be enriched in the extractive solvent are already described by way of example in EP-A 0 329 958 and comprise, for example, hemellitol, p-cymene, 1,2-diethylbenzene, indane, durene, isodurene, trimethylbenzene, naphthalene, methylnaphthalenes, dimethylnaphthalenes and diphenyl. In addition, however, oligomeric and polymeric aromatics with a very high boiling point, also referred to for short hereinafter as "ultrahigh boilers", which may have interface-active properties, also accumulate in the extractive solvent. It has been found that such "ultrahigh boilers" with apparently interface-active properties accumulate in the extractive solvent, and that the presence of these oligo- or polyaromatics apparently hinders the phase separation in step (E) into an aqueous extract phase and an organic high boiler phase. It has additionally been found that the problem can be remedied when the performance of step (E) is preceded by removal of the oligomeric and polymeric aromatics ("ultrahigh boilers") at least partly from the extractive solvent by distillation.

In a preferred embodiment, performance of step (E) is preceded by performance of a distillation in which a fraction composed of very high-boiling hydrocarbons ("ultrahigh boilers") is removed from the substream d1 of the extractive solvent.

The ultrahigh boilers are generally removed under a reduced pressure of from 10 to 100 mbar in a distillation column having from 1 to 10 theoretical plates. The top temperature is generally in the range from 100 to 170° C., the bottom temperature in the range from 120 to 190° C. The ultrahigh boilers are obtained as a highly viscous bottom product which can be evaporated without decomposition. In general, the oligomeric and polymeric ultrahigh boilers are depleted by this distillation step to an extent of at least 90%, preferably to an extent of at least 95%.

In general, in the process according to the invention, hydrocarbon mixtures composed of aliphatic, cycloaliphatic and aromatic hydrocarbons are used, which have boiling points in the range from 50 to 225° C. at atmospheric pressure. These generally comprise a total of from 10 to 90% by weight of toluene and xylenes and/or a total of from 10 to 90% by weight of benzene, toluene and xylenes. In addition, the hydrocarbon mixtures generally comprise aliphatic hydrocarbons having from 5 to 10 carbon atoms and possibly cycloaliphatic hydrocarbons having from 5 to 10 carbon atoms. Typical hydrocarbon mixtures which can be worked up in accordance with the invention are, for example, reformat gasolines and pyrolysis gasolines. The high boilers present in the hydrocarbon mixture, which accumulate in the extractive solvent and can be removed economically therefrom by distillation only with difficulty, if at all, generally have boiling points in the range from 170 to 250° C. The very high-boiling hydrocarbons ("ultrahigh boilers") also present therein generally have a boiling point above 240° C. at atmospheric pressure or cannot be distilled at all without decomposition, not even under reduced pressure.

The hydrocarbon mixture a1 is subjected to an extractive distillation with N-formylmorpholine as the extractive solvent. The operating conditions in the extractive distillation column are generally selected as described in: Ullmanns Encyclopedia of Industrial Chemistry, chapter: Benzene, Wiley-VCH GmbH, 2002.

In this extractive distillation, toluenes and xylenes or benzene, toluene and xylenes accumulate in the extractive solvent and are generally drawn off with it from the bottom of the extractive distillation column, while the nonaromatic hydrocarbons substantially freed from the aromatic hydrocarbons are generally obtained at the top of the extractive distillation column. The mixture of extractive solvent and aromatic hydrocarbons, which also comprises the high boilers and ultrahigh boilers, is subsequently separated by distillation into one or more aromatics fractions which are obtained as top draw streams and/or side draw streams, and the extractive solvent which comprises the high and ultrahigh boilers and is generally obtained at the bottom of the distillation column. When, for example, the hydrocarbon mixture a1 comprises benzene, toluene and xylenes, a fraction c11 comprising benzene as the top draw stream and a fraction c12 comprising toluene and a further fraction c13 comprising xylenes as side draw streams can be maintained in the distillative separation of the extractive solvent/aromatics mixture b1 in step (C). When the hydrocarbon mixture a1 comprises, for example, essentially toluene and xylene as aromatic hydrocarbons, essentially toluene as the top draw stream and xylenes as the side draw stream can be obtained in the distillative separation of the extractive solvent/aromatics mixture b1. However, it is also possible to obtain a mixture of toluene and xylene, which may possibly also comprise ethylbenzene, as the top draw stream.

From the extractive solvent c2 which has been recovered by distillation and comprises the high and ultrahigh boilers, the main stream is recycled into the extractive distillation (B). In order to prevent accumulation of the high boilers in the extractive solvent and hence a continuous deterioration in the extractive solvent quality, a substream d1 of the extractive solvent is removed to remove the high boilers present therein. This substream comprises generally from 0.01 to 10%, preferably from 0.1 to 2%, of the total stream of the extractive solvent c2 obtained by distillation in step (C). The removal of the extractive solvent from the high boilers present therein is effected in step (E) by extraction of the extractive solvent with water. To this end, the substream d1 of the extractive solvent comprising the high boilers can be transferred to a mixing unit and dispersed with water to form an aqueous extract phase e1 essentially free of high boilers, and an organic phase e2 comprising the high boilers. The phases are subsequently separated in a phase separation apparatus which may be identical to the mixing unit or be a phase separation apparatus different therefrom. The extractive solvent is contacted intensively with water, such that the thermodynamic equilibrium between the aqueous extract phase which forms on the one hand and the organic phase on the other hand can be established. Suitable dispersing units are stirred vessels, static mixers, mixing pumps and dynamic mixers. It is also possible to perform the extraction in a countercurrent column.

The extractive solvent is fully miscible with water. The high-boiling impurities from aromatic and nonaromatic hydrocarbons are of sparing solubility in water, such that addition of water to the extractive solvent contaminated with the high-boiling hydrocarbons forms a second liquid, organic phase which consists mainly of these impurities. The two phases have a sufficiently great density difference that they can be separated from one another in commercial apparatus for liquid/liquid phase separation. Suitable phase separation apparatus include phase separators, centrifuges, coalescence phase separators and others. The extraction with water and subsequent phase separation can be carried out either in one stage, for example in a mixer-settler, or in more than one stage, for example in a mixer-settler battery or a countercurrent column. The temperature has an influence on the miscibility gap, which is caused by the addition of water to the extractant comprising the high boilers. In principle, temperatures above 100° C. are possible when the extraction with water is carried out in a pressure apparatus. Possible temperatures are in the range from 0 to 160° C. However, preferred temperatures are between 10 and 90° C.; particularly favorable temperatures have been found to be between 40 and 60° C. An amount of water at least sufficiently great that separated liquid phases form is added. The amount of water:amount of extractive solvent ratio is generally from 0.05 to 5 kg/kg, more preferably from 0.2 to 0.5 kg/kg.

An aqueous extract phase e1 essentially free of high boilers and an organic phase e2 which comprises the high boilers or essentially consists thereof are obtained.

The resulting aqueous extract phase e1 essentially freed of high boilers is subsequently distilled to recover the extractive solvent in purified form. This distillation can be carried out as described in EP-A 0 329 958. In this case, the extractive solvent/water mixture is distilled together with the nonaromatic hydrocarbons removed in step (B), the water present in the extractive solvent/water mixture generally being distilled off azeotropically together with the nonaromatic hydrocarbons via the top of the distillation column. From this azeotropic mixture, water is removed by phase separation and, if appropriate, recycled into the high boiler removal step (E). The extractive solvent freed of water can be separated by phase separation from entrained nonaromatic hydrocarbons and be recycled into the extractive distillation (B).

FIG. 1 shows a preferred embodiment of the process according to the invention.

The hydrocarbon mixture 1 comprising benzene, toluene, xylene and nonaromatic hydrocarbons, and the extractive solvent 2, are fed into the extractive distillation column 3. At the top of the extractive distillation column, a mixture 4 of nonaromatic hydrocarbons and extractive solvent is drawn off and is separated in the downstream distillation column 5 into the nonaromatic hydrocarbons 6 and the extractive solvent 7. In the bottom of the extractive distillation column, a mixture 8 of extractive solvent and the aromatic hydrocarbons is obtained. From this mixture, the individual aromatics fractions of benzene 10, toluene 11 and xylene 12 are then removed by distillation in a distillation column 9. From the extractive solvent stream 13 obtained at the bottom of the distillation column 9, which also comprises the high and ultrahigh boilers, the main stream 14 is recycled into the extractive distillation column 3. A substream 15 is removed to remove the high boilers present therein. From this substream 15, oligomeric and polymeric ultrahigh boilers with interface-active properties are removed in the distillation column 16 as residue 17. The extractive solvent stream 18 which has been freed of the ultrahigh boilers and still comprises the high boilers is transferred together with water 19 into the dispersion unit 20. The resulting dispersion 21 is separated in the phase separation apparatus 22 into an organic upper phase 23 which comprises the high boilers, and an aqueous lower phase 26 which comprises the extractive solvent. A portion 24 of the organic upper phase is discharged from the process; the other portion 25 is recycled into the dispersion unit 20. The aqueous lower phase 26 is separated in a downstream distillation column 27 into a water stream 28 which is discharged from the process, and the purified extractive solvent stream 29 which is recycled into the extractive distillation column 3.

Figure 2:
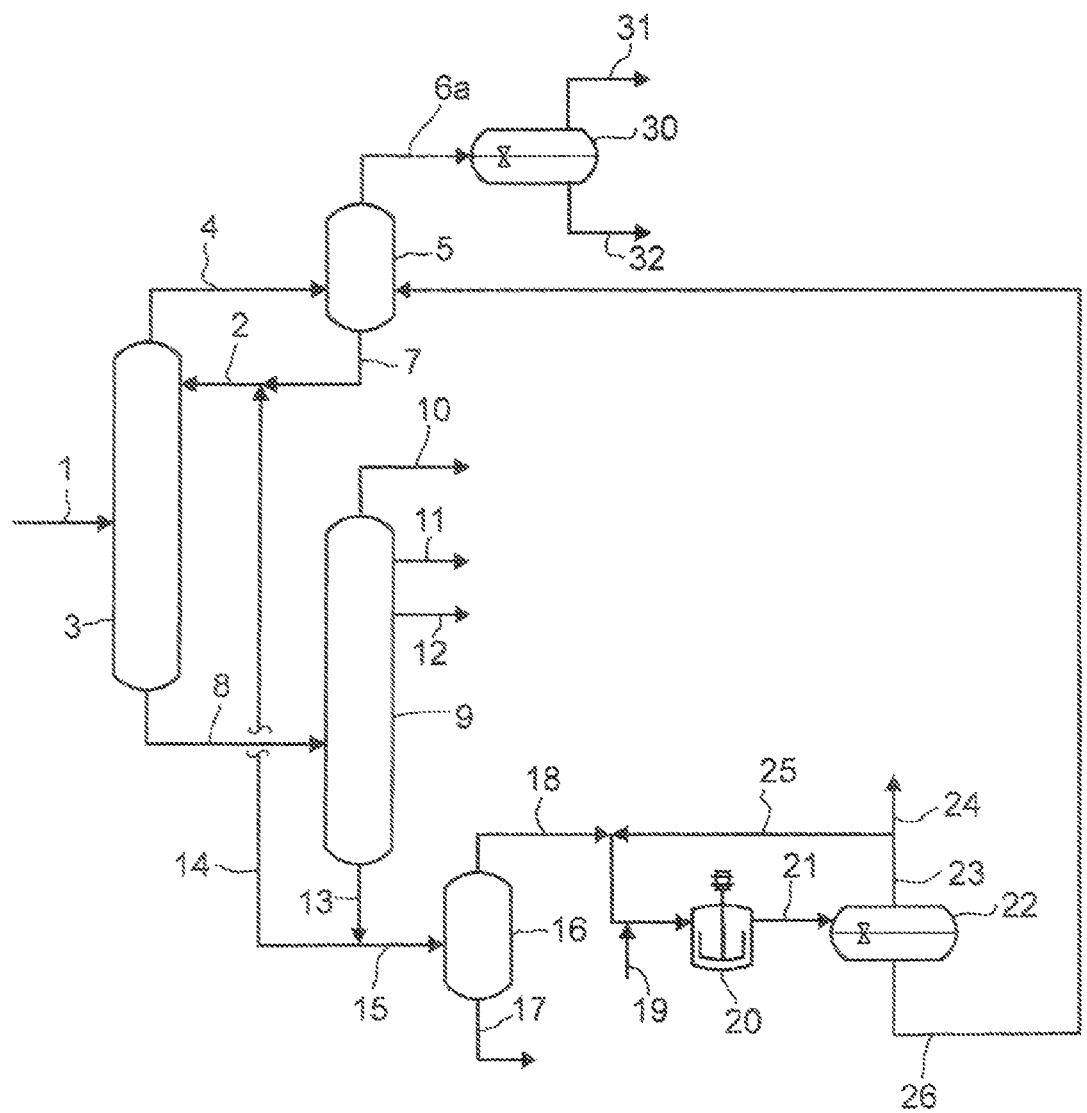

FIG. 2 shows a further preferred embodiment of the process according to the invention.

FIG. 2 shows a variant of the process illustrated in FIG. 1. In this variant, the aqueous lower phase 26 which comprises the extractive solvent and is obtained in the phase separation apparatus 22 is not distilled in a separate distillation column, but rather distilled together with the fraction which is obtained as the top draw stream 4 and is composed of nonaromatic hydrocarbons in the distillation column 5. The top draw stream 6a obtained is a mixture of nonaromatic hydrocarbons and water, which is separated in the downstream phase separation apparatus 30 into an organic upper phase composed of nonaromatic hydrocarbons 31 and an aqueous lower phase 32. The aqueous lower phase can be recycled (as stream 19) into the phase separation apparatus 20.

The invention is illustrated in detail by the examples which follow.

COMPARATIVE EXAMPLE 1

In a continuous mixer-settler, 20 kg/h of NFM were dispersed at 40° C. with 15.2% by weight of hydrocarbons ("raffinate", comprising 17% by weight of $C_9^+$ hydrocarbons, 34% by weight of tetralin, 18% by weight of naphthalene, 1.6% by weight of alkylnaphthalenes and 1.6% by weight of diphenyl) and 10 kg/h of water, and the two phases obtained were separated in the phase separator. Another approx. 1.9% by weight of hydrocarbons remained in the aqueous NFM phase. The depletion of hydrocarbons was thus only approx. 87% owing to inadequate phase separation.

EXAMPLE 1

In the same apparatus, an experiment was performed at 40° C., in which 5 kg/h of water as an extractant and 25 kg/h of NMF which had been adjusted with raffinate (composition as described above under comparative example 1) to a hydrocarbon content of 68% by weight, in order to simulate the conditions of internal recycling of the organic phase, were mixed. Only another approx. 0.5% by weight of the hydrocarbons remained in the aqueous NFM phase; the depletion was thus 96%.

The examples show that the recycling of the organic phases leads to an improvement in the phase separation and hence to a higher depletion of the high boilers.

COMPARATIVE EXAMPLE 2

807 g of NFM which comprised 22% by weight of high-boiling impurities and had not been distilled beforehand were dispersed in a stirred vessel with 404 g of demineralized water at 40° C. for 10 minutes. 10 minutes after the stirrer had been switched off, the two liquid phases in the stirred vessel were assessed visually. The light organic upper phase was completely permeated with crud.

EXAMPLE 2

4 l of N-formylmorpholine (NFM) laden with high boilers were distilled off via the top of the column under a reduced pressure of approx. 48 mbar and at oil bath temperature approx. 180° C. The top temperature was from 105 to 120° C. After approx. 4 hours, approx. 0.1% by weight of high boilers remained in the bottom. The characterization of the black bottom product, which was not evaporable without decomposition and was highly viscous at room temperature, showed approx. 0.01% by weight of coke, polymers and approx. 0.05% by weight of high-boiling aromatics which were difficult to identify. The high boilers were discharged from the process and sent to incineration as residue. The N-formylmorpholine freed of high boilers was subsequently extracted with water. If the high boilers were not removed, this led, in the extraction step in the phase separation, to a stable crud layer in the organic phase, which greatly complicated the operation of a phase separator. When, in contrast, the NFM purified to remove ultrahigh boilers was used, the organic phase after the extraction of the NMF with water was clear.

EXAMPLE 3

778 g of NFM which had been distilled and, after distillative purification, still comprised approx. 20% by weight of high-boiling aromatics were dispersed at 40° C. in a stirred vessel with 389 g of demineralized water for 10 minutes. 10 minutes after the stirrer had been switched off, the two liquid phases were assessed visually in the stirred vessel. The light organic upper phase was clear.

The examples show that, in the extractive purification of NFM by dispersion with water and subsequent phase separation, a significantly better phase separation is achieved when the NFM comprising the high boilers has been freed of polymeric ultrahigh boilers beforehand by distillation.

COMPARATIVE EXAMPLE 3

802 g of NFM which, after distillation, comprised 15.2% by weight of high-boiling aromatics were dispersed at 40° C. in a stirred vessel with 401 g of demineralized water for 10 minutes. After the stirrer had been switched off, a separating rate of the dispersion of 10 mm/min was determined. The aqueous lower phase was slightly cloudy, and the dispersion layer remained in the stirred vessel.

EXAMPLE 4

112 g of NFM which, after distillative purification, still comprised 15.2% by weight of high-boiling aromatic hydrocarbons, and 687 g of organic high boilers (organic upper phase of the phase separator) were dispersed at 40° C. in a stirred vessel with 399 g of demineralized water for 10 minutes. After the stirrer had been switched off, a separation rate of the dispersion of 66 mm/min was determined. The aqueous lower phase was clear, and no dispersion layer was present in the stirred vessel.

EXAMPLE 5

In a continuous mixer-settler, 20 kg/h of the organic phase composed of aromatic high boilers from the extractive purification of NFM with water (the high boiler phase having comprised 0.86% by weight of NFM) and 10 kg/h of demineralized water were dispersed at 40° C., and the two phases obtained were separated in a phase separator. The depletion of the NFM from the organic phase was 94%.

It has been found that, surprisingly, it is possible to recover, by extraction with water, from the organic phase obtained in the extractive purification of the NFM, the NFM which is dissolved therein and has been entrained by droplet entrainment.

The invention claimed is:

1. A process for obtaining aromatic hydrocarbons selected from benzene, toluene, xylene and ethylbenzene and mixtures thereof from a hydrocarbon mixture which additionally comprises nonaromatic hydrocarbons and high boilers, comprising the steps of
    (A) providing a hydrocarbon mixture a1 and an extractive solvent a2 composed of N-formylmorpholine,
    (B) extractively distilling the hydrocarbon mixture a1 with the extractive solvent to obtain a mixture b1 of extractive solvent and the aromatic hydrocarbons, said mixture comprising high boilers, and a mixture b2 comprising nonaromatic hydrocarbons,
    (C) distilling the mixture b1 of extractive solvent and aromatic hydrocarbons obtained in step (B) to obtain one or more fractions c1 composed of aromatic hydrocarbons and the extractive solvent c2 which comprises high boilers,
    (D) removing a substream d1 from the extractive solvent c2 and recycling the extractive solvent c2 into the extractive distillation (B),
    (E) extracting the substream d1 of the extractive solvent with water to obtain an aqueous extract phase e1 essentially free of high boilers and an organic phase e2 comprising the high boilers,
    (F) distilling the aqueous extract phase e1 and recovering the extractive solvent a2 in purified form, and recycling the extractive solvent into the extractive distillation (B), which comprises removing a substream e2' from the organic phase e2 comprising the high boilers and recycling it into the extraction of step (E), the amount of the organic phase e2' thus circulated being such that, where the substream d1 composed of extractive solvent comprising high boilers, water and circulated stream e2' is dispersed, the aqueous extract phase e1 essentially freed of high boilers forms as a disperse phase, and the organic phase composed of high boilers e2 form as a continuous phase.

2. The process according to claim 1, wherein performance of step (E) is preceded by performance of a distillation in which a fraction composed of very high-boiling hydrocarbons is removed from the substream d1 of the extractive solvent.

3. The process according to claim 2, wherein at least 90% of the very high-boiling hydrocarbons are removed by distillation.

4. The process according to claim 1, wherein the hydrocarbon mixture comprises benzene, toluene and xylene, and, in step (C), a fraction c11 comprising benzene, a fraction c12 comprising toluene, and a fraction c13 comprising xylenes are obtained.

5. The process according to claim 1, wherein the hydrocarbon mixture comprises toluene and xylene, and, in step (C), a fraction c11 comprising toluene, and a fraction c12 comprising xylenes are obtained.

6. The process according to claim 1, wherein the very high-boiling hydrocarbons are removed by distillation under a reduced pressure of from 10 to 500 mbar in a distillation column having from 1 to 10 theoretical plates.

* * * * *